US011497452B2

(12) United States Patent
Cheung et al.

(10) Patent No.: US 11,497,452 B2
(45) Date of Patent: Nov. 15, 2022

(54) PREDICTIVE KNEE JOINT LOADING SYSTEM

(71) Applicant: The Hong Kong Polytechnic University, Hong Kong (CN)

(72) Inventors: Tsz Hei Cheung, Hong Kong (CN); Ho Man Chan, Hong Kong (CN); Kevin Ki Wai Ho, Hong Kong (CN); Zoe Yau Shan Chan, Hong Kong (CN); Hanwen Zhang, Hong Kong (CN); Man Fung Lam, Hong Kong (CN); Chao Wang, Hong Kong (CN); Sizhong Wang, Hong Kong (CN); Shuotong Wang, Hong Kong (CN); Xiaoyu Wei, Hong Kong (CN); Akash Malhotra, Hong Kong (CN); Chun Kwan Ching, Hong Kong (CN)

(73) Assignee: The Hong Kong Polytechnic University, Kowloon (CN)

( * ) Notice: Subject to any disclaimer, the term of this patent is extended or adjusted under 35 U.S.C. 154(b) by 140 days.

(21) Appl. No.: 16/447,636

(22) Filed: Jun. 20, 2019

(65) Prior Publication Data
US 2020/0397384 A1    Dec. 24, 2020

(51) Int. Cl.
*A61B 5/00* (2006.01)
*A61B 5/11* (2006.01)
(Continued)

(52) U.S. Cl.
CPC ............ *A61B 5/7275* (2013.01); *A61B 5/112* (2013.01); *A61B 5/6829* (2013.01);
(Continued)

(58) Field of Classification Search
None
See application file for complete search history.

(56) References Cited

U.S. PATENT DOCUMENTS 10,105,571 B2 * 10/2018 Solinsky ............... A61B 5/375
10,842,415 B1 * 11/2020 Jagannathan ...... A63B 24/0062
(Continued)

FOREIGN PATENT DOCUMENTS

| CN | 105852866 A | * | 8/2016 |
| JP | 2017202236 A | * | 11/2017 |

OTHER PUBLICATIONS

CN-105852866-A Machine Translation (Year: 2016).*
(Continued)

*Primary Examiner* — Sean P Dougherty
*Assistant Examiner* — Benjamin S Melhus
(74) *Attorney, Agent, or Firm* — Millen, White, Zelano & Branigan, P.C.; William Nixon; Wan-Ching Montfort

(57) ABSTRACT

The present disclosure describes a system, method and software applications for predicting the KAM of a subject for a plurality of gait cycles of a subject. At least one sensor attachable adjacent to the ankle of at least one leg of the subject provides accelerometer and gyroscopic data for the plurality of gait cycles. A processing means receives subject parameters and accelerometer and gyroscopic data from the at least one sensor for evaluation by a neural network of predicted KAM values for the plurality of gait cycles of the subject. The neural network is configured via determining KAM values for each of the plurality of subjects from measurements during a plurality of gait cycles and other parameters.

10 Claims, 10 Drawing Sheets

(51) Int. Cl.
    *G16H 50/20* (2018.01)
    *G16H 20/30* (2018.01)
(52) U.S. Cl.
    CPC .......... *A61B 5/7264* (2013.01); *A61B 5/7278* (2013.01); *A61B 5/746* (2013.01); *G16H 20/30* (2018.01); *G16H 50/20* (2018.01); *A61B 2562/0219* (2013.01)

(56) References Cited

U.S. PATENT DOCUMENTS

| | | | | |
|---|---|---|---|---|
| 2003/0144710 | A1* | 7/2003 | Haugland | A61F 2/72 607/48 |
| 2011/0270132 | A1* | 11/2011 | Mezghani | A61B 5/1038 600/587 |
| 2013/0217998 | A1* | 8/2013 | Mahfouz | A61B 8/4263 600/409 |
| 2013/0244211 | A1* | 9/2013 | Dowling | G16H 20/30 434/247 |
| 2015/0045700 | A1* | 2/2015 | Cavanagh | A61B 5/4528 600/595 |
| 2017/0042467 | A1* | 2/2017 | Herr | A61B 5/7271 |
| 2017/0238845 | A1* | 8/2017 | Wei | A61B 5/6829 |
| 2018/0060511 | A1* | 3/2018 | Sato | G16H 50/20 |
| 2018/0235830 | A1* | 8/2018 | Rokosz | A61H 3/00 |
| 2019/0117156 | A1* | 4/2019 | Howard | A61B 5/4585 |
| 2020/0054249 | A1* | 2/2020 | Fukushi | A61B 5/1036 |
| 2020/0093400 | A1* | 3/2020 | Hamner | A61N 1/36031 |
| 2021/0186436 | A1* | 6/2021 | Fukushi | A61B 5/4528 |
| 2021/0369143 | A1* | 12/2021 | Ferber | G16H 50/20 |

OTHER PUBLICATIONS

Favre, Julien, et al. "A neural network model to predict knee adduction moment during walking based on ground reaction force and anthropometric measurements." Journal of biomechanics 45.4 (2012): 692-698. (Year: 2012).*

Y. Shen et al., "A wearable sensor system for knee adduction moment measurement," 2016 IEEE International Conference on Real-time Computing and Robotics (RCAR), 2016, pp. 7-12, doi: 10.1109/RCAR.2016.7783992. (Year: 2016).*

JP2017202236A Machine Translation (Year: 2017).*

Z. He, T. Liu and J. Yi, "A Wearable Sensing and Training System: Towards Gait Rehabilitation for Elderly Patients With Knee Osteoarthritis," in IEEE Sensors Journal, vol. 19, No. 14, pp. 5936-5945, Jul. 15, 2019, doi: 10.1109/JSEN.2019.2908417. (Year: 2019).*

T.P. Andriacchi et al., "A Framework for the in Vivo Pathomechanics of Osteoarthritis at the Knee", Annals of Biomedical Engineering, vol. 32, No. 3 (Mar. 2004) pp. 447-457.

J. Bae et al., "A Soft Exosuit for Patients with Stroke: Feasibility Study with a Mobile Off-Board Actuation Unit", 2015 IEEE International Conference on Rehabilitation Robotics (ICORR) (2015) pp. 131-138.

T. Chen et al., "XGBoost: A Scalable Tree Boosting System", Proceedings of the 22nd ACM SIGKDD International Conference on Knowledge Discovery and Data Mining (2016) pp. 785-794.

B. Jackson et al., "Immediate and Short-Term Effects of Real-Time Knee Adduction Moment Feedback on the Peak and Cumulative Knee Load During Walking", Journal of Orthopaedic Research, vol. 36, No. 1 (2018) pp. 397-404.

T. Miyazaki et al., "Dynamic Load at Baseline Can Predict Radiographic Disease Progression in Medial Compartment Knee Osteoarthritis", Annals of the Rheumatic Diseases, vol. 61, No. 7 (2002) pp. 617-622.

V. Nair et al., "Rectified Linear Units Improve Restricted Boltzmann Machines", Proceedings of the 27th International Conference on Machine Learning (ICML-10) (2010) pp. 807-814.

A. Banks et al., "OASIS Standard" MQTT Version 3.1.1 (2014).

S.J. Pan et al., "A Survey on Transfer Learning" IEEE Transactions on Knowledge and Data Engineering, vol. 22, No. 10 (2010) pp. 1345-1359.

L. Sharma et al., "Knee Adduction Moment, Serum Hyaluronan Level, and Disease Severity in Medial Tibiofemoral Osteoarthritis", Arthritis & Rheumatism, vol. 41, No. 7 (1998) pp. 1233-1240.

P.B. Shull et al., "Six-Week Gait Retraining Program Reduces Knee Adduction Moment, Reduces Pain, and Improves Function for Individuals with Medial Compartment Knee Osteoarthritis", Journal of Orthopaedic Research, vol. 31, No. 7 (2013) pp. 1020-1025.

N. Srivastava et al., "Dropout: A Simple Way to Prevent Neural Networks From Overfitting", Journal of Machine Learning Research, vol. 15, No. 1 (2014) pp. 1929-1958.

L.E. Thorp et al., "Relationship Between Pain and Medial Knee Joint Loading in Mild Radiographic Knee Osteoarthritis", Arthritis & Rheumatism, vol. 57, No. 7 (2007) pp. 1254-1260.

T. Tieleman et al., "Lecture 6.5-rmsprop: Divide the Gradient by a Running Average of its Recent Magnitude" Coursera: Neural Networks for Machine Learning, vol. 4, No. 2 (2012) pp. 26-31 (https://www.youtube.com/watch?v=defQQqkXEfE).

\* cited by examiner

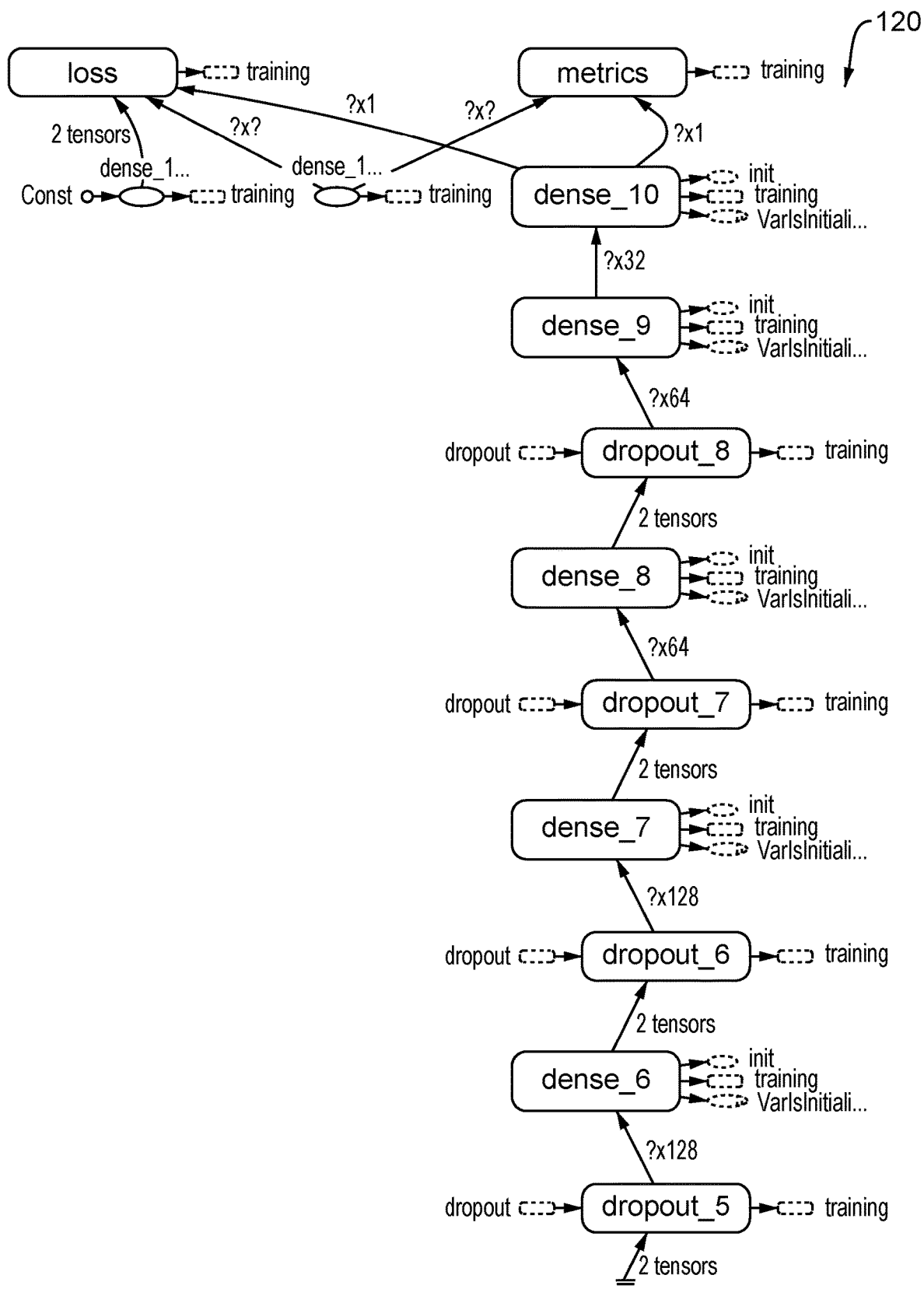
Fig. 5b1

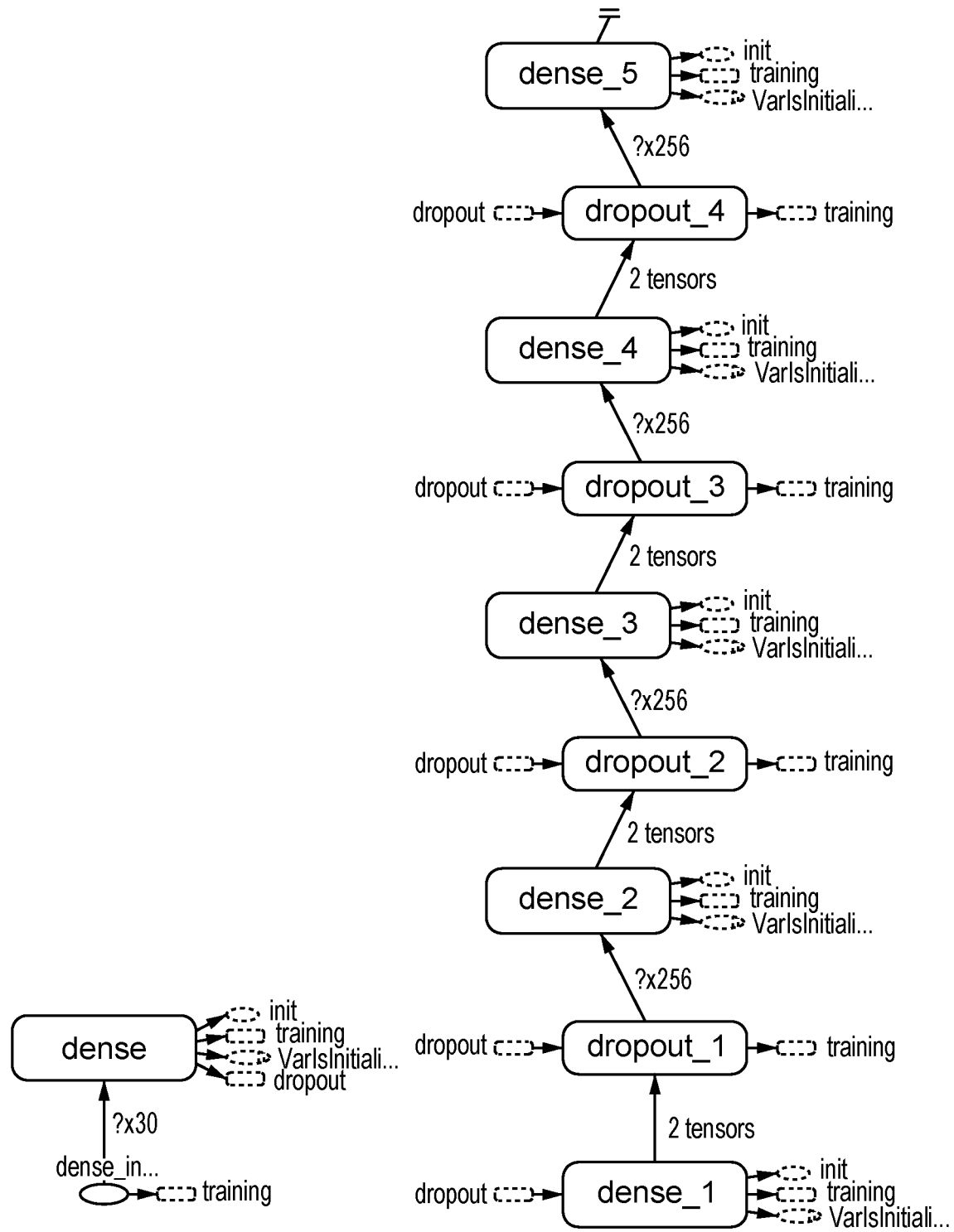
Fig. 5b2

PREDICTIVE KNEE JOINT LOADING SYSTEM

FIELD

The present disclosure is directed to a predictive knee joint loading system and method, especially for determining knee joint loading in patients with knee osteoarthritis.

BACKGROUND

Knee osteoarthritis (knee OA) is a common chronic orthopaedic health issue. The severity of knee OA normally increases with age, causing significant impact on lifestyle including impacts on overall mobility, occupational issues, enjoyment of life and economic pressures.

Decreasing joint load (force put on a weight-bearing or load-bearing joint during activity) may assist in relieving knee osteoarthritis. Knee adduction moment (KAM) is an important measurement for characterizing knee joint loading. Currently, KAM can only be determined by measuring the subject in a clinic with sophisticated and expensive laboratory equipment and a serious of tedious steps. Typically such laboratory based measurements require multiple cameras for tracking various reflective markers which must be accurately fitted to a subject; force plates and detailed analysis of results obtained. Such in-clinic measurements are not convenient for subjects and cannot provide KAM measurements to the subject in such a way as to provide them feedback for decreasing joint load during various normal everyday walking and other activities outside a laboratory setting.

Therefore, there is a need for a system which can measure or predict KAM in a subject outside the laboratory environment which addresses or at least ameliorates some of the above problems and disadvantages.

SUMMARY

According to one aspect of the present disclosure, there is a system for predicting KAM of a subject for a plurality of gait cycles of the subject, the system comprises: at least one sensor attachable adjacent the ankle of at least one leg of the subject for providing accelerometer and gyroscopic data for the plurality of gait cycles; and a processing means for receiving parameters of the subject and accelerometer and gyroscopic data from the at least one sensor for evaluation by a neural network of predicted KAM for the plurality of gait cycles of the subject, the neural network is configured via determining KAM for a plurality of gait cycles of a plurality of subjects from measurements during the plurality of gait cycles and parameters from said plurality of subjects.

The measurements used for configuring the neural network may include accelerometer and gyroscopic data from at least one sensor and measured KAM for the plurality of gait cycles of the plurality of subjects. The parameters of the subject and the parameters from the plurality of subjects may comprise one or more parameters selected from the group comprising age, gender, body mass, height, knee width, ankle width, and leg identity.

The measured KAM may be determined from kinematic information for each of the plurality of subjects over the plurality of gait cycles for that subject and corresponding ground reaction force measurements.

Optionally, the at least one sensor is an inertial measurement unit sensor locatable proximal to the level of the malleolus and adjacent to the ankle and configured to provide accelerometer and gyroscopic data during the plurality of gait cycles of the subject.

Preferably, the sensor is located in a receiving pocket of a shoe configured to maintain the sensor adjacent the lateral malleolus during a gait cycle.

The system further comprises a portable electronic device in communication with the processing means for receiving and displaying predicted KAM during the plurality of gait cycles of the subject to the subject. The processing means may be further configured to generate a signal to alert the subject when the predicted KAM values for that subject in a gait cycle exceeds a predetermined threshold. Optionally, the processing means may be configured for extracting a plurality of data segments from the accelerometer and gyroscopic data of the at least one sensor between the heel strike and toe off parts of a gait cycle.

Optionally, the predicted KAM for a subject for a gait cycle is outputted from the neural network before a next gait cycle of the subject.

The neural network is optimised for predicting KAM for a specific subject for a plurality of gait cycles other than a first plurality of gait cycles, wherein the neural network is updated by determining KAM using kinematic information over a first plurality of gait cycles for that specific subject and corresponding ground reaction force measurements and accelerometer and gyroscopic data from the at least one sensor for the specific subject over said first plurality of gait cycles.

According to another aspect of the present disclosure, there is a method of training a neural network for predicting the KAM of a subject for a plurality of gait cycles of the subject, the method comprises: storing measured KAM and accelerometer and gyroscopic data from at least one sensor attachable adjacent the ankle of at least one leg of each of a plurality of subjects over a plurality of gait cycles of each of the plurality of subjects; deriving values from the stored accelerometer and gyroscopic data from the sensor for the plurality of gait cycles of each of a plurality of subjects; and training the neural network for a predetermined number of cycles using the derived values over the plurality of gait cycles of each of the plurality of subjects, corresponding measured KAM and predicted KAM over the plurality of gait cycles of each of the plurality of subjects, and the parameters of the plurality of subjects wherein the neural network is adjusted after one or more training cycles to minimise the sum of the absolute value of differences between predicted KAM and measured KAM of corresponding cycles.

The measured KAM is determined from kinematic information for each of the plurality of subjects over the plurality of gait cycles for that subject and corresponding ground reaction force measurements.

Optionally, the randomness of the accelerometer and gyroscopic data is increased by normalizing and/or randomly shuffling.

The method further comprises calibrating the neural network from measured KAM and accelerometer and gyroscopic data from the at least one sensor for a plurality of gait cycles of further one or more subjects and parameters of the further one or more subjects, wherein the calibration is based on mean and standard deviation of data used in training and calibrating; and the accelerometer and gyroscopic data from the at least one sensor for the plurality of gait cycles of the further one or more subjects are normalized and/or randomly shuffled.

According to a further aspect of the present disclosure, there is a software application executable on one or more processors for predicting for one or more gait cycles of a subject during walking, the software application being configured for receiving on a portable electronic device parameters of the subject and accelerometer and gyroscopic data from at least one sensor attachable adjacent the ankle of at least one leg of the subject for evaluation by a neural network of predicted KAM for the plurality of gait cycles of the subject; processing the accelerometer and gyroscopic data to extract therefrom a plurality of data segments including peak KAM in the gait cycles of the subject; transmitting the plurality of extracted data segments to a neural network operable on one or more remotely located processors configured for generating a predicted KAM from received accelerometer and gyroscopic data and parameters of the subject wherein the neural network is configured via determining KAM for a plurality of gait cycles of a plurality of subjects from measurements during the plurality of gait cycles and parameters from said plurality of subjects; and outputting predicted KAM for the plurality of gait cycles of the subject for displaying during the gait cycles of the subject on the portable electronic device.

According to still another aspect of the present disclosure, there is a software application executable on a portable electronic device for predicting KAM for a plurality of gait cycles of a subject, the software application being configured for receiving parameters of the subject and accelerometer and gyroscopic data from at least one sensor attachable adjacent the ankle of at least one leg of the subject for a plurality of gait cycles for evaluation by a neural network of predicted KAM for the plurality of gait cycles of the subject; processing the accelerometer and gyroscopic data to extract therefrom a plurality of data segments including peak KAM in the gait cycles of the subject; generating on a processor of the portable electronic device, a neural network configured via determining KAM for a plurality of gait cycles of a plurality of subjects from measurements during the plurality of gait cycles and parameters from said plurality of subjects; and transmitting the plurality of extracted data segments to the neural network to output from the neural network a predicted KAM to a display of the portable electronic device from the plurality of extracted data segments for the subject for the plurality of gait cycles.

According to still further aspect of the present disclosure, there is a method for predicting the KAM for a plurality of gait cycles of a subject, the method comprises: providing accelerometer and gyroscopic data for the plurality of gait cycles from at least one sensor attachable adjacent to the ankle of at least one leg of the subject; and receiving parameters of the subject and accelerometer and gyroscopic data from the at least one sensor for evaluation by a neural network of predicted KAM for the plurality of gait cycles of the subject, wherein the neural network is configured via determining KAM for a plurality of gait cycles of a plurality of subjects from measurements during the plurality of gait cycles and parameters from said plurality of subjects.

The measurements used for configuring the neural network include accelerometer and gyroscopic data from at least one sensor and measured KAM for the plurality of gait cycles for the plurality of subjects. The parameters from the plurality of subjects comprise one or more parameters selected from the group comprising age, gender, body mass, height, knee width, ankle width, and leg identity.

The measured KAM is determined from kinematic information for each of the plurality of subjects over the plurality of gait cycles for that subject and corresponding ground reaction force measurements.

Optionally, the at least one sensor is an inertial measurement unit sensor locatable proximal to the level of the malleolus and adjacent to the ankle and configured to provide accelerometer and gyroscopic data during the plurality of gait cycles of the subject.

The method further comprises receiving and displaying predicted KAM during the plurality of gait cycles of the subject on a portable electronic device.

The method further comprises generating a signal to alert the subject when the predicted KAM during the plurality of gait cycles of the subject exceeds a predetermined threshold.

Optionally, the predicted KAM for a subject for a gait cycle is outputted from the neural network before a next gait cycle of the subject.

BRIEF DESCRIPTION OF THE DRAWINGS

The above and other features of the present disclosure, its nature and advantages will be apparent upon consideration of the following description and with reference to embodiment(s) depicted in the accompanying drawings, in which:—

FIG. 5b1 depicts an exemplary architecture of the artificial neural network of FIG. 5a.

FIG. 5b2 depicts an exemplary architecture of the artificial neural network of FIG. 5a.

FIG. 5c depicts a training graph for the second exemplary machine learning algorithm of FIG. 5a.

FIG. 5d depicts the transfer learning curve for the second exemplary machine learning algorithm of FIG. 5a.

DETAILED DESCRIPTION OF THE PREFERRED EMBODIMENTS

The disclosure provides a method and system for predicting KAM for a subject during walking, using a trained machine learning model based on data obtained from sensors located proximal to the subject's ankles. Advantageously, the system and method of predicting KAM can enable a subject to receive predicted KAM arising from walking and other activities being performed even when outside the laboratory in real-time or almost real-time; so that the subject can make subtle adjustments to their gait pattern and thereby reduce KAM.

Figure 1:
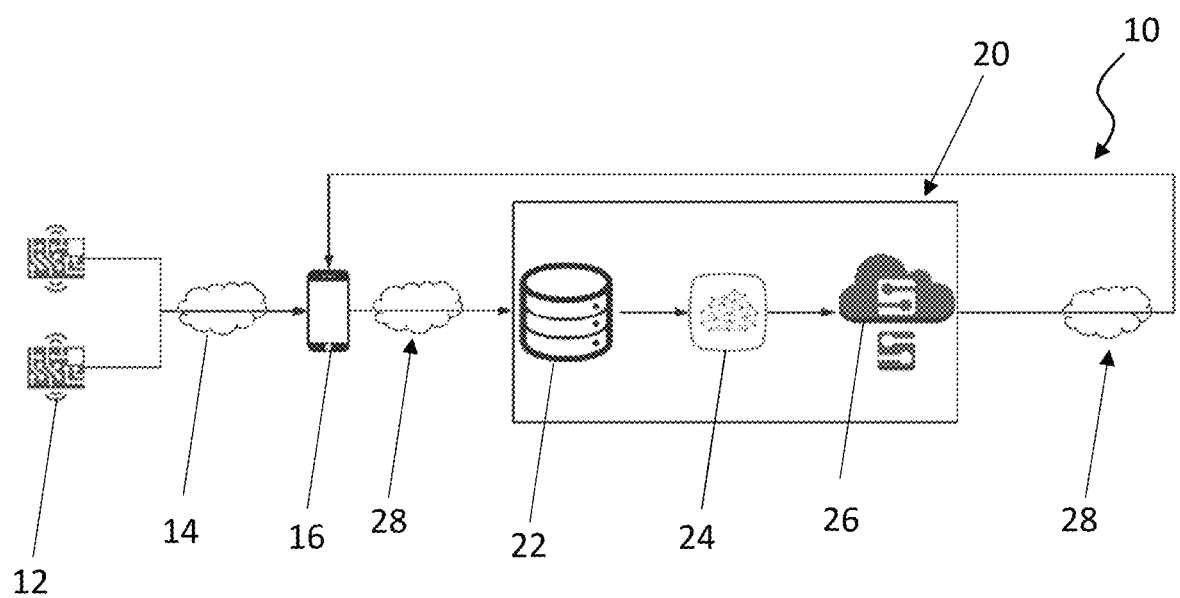
FIG. 1 depicts the schematic architecture of an embodiment of the present disclosure.

FIG. 1 depicts the schematic architecture 10 of an embodiment of the present disclosure.

As shown and discussed in more detail below, the KAM for a subject can be predicted from data obtained from sensor 12 located proximal the ankles of the subject, and interpreted via a trained neural network.

Preferably the sensor 12 may be an inertial measurement unit (IMU) which includes accelerometer and gyroscope which provide data during various positions in the gait cycle for a subject when he/she is walking or running. The sensor 12 may be communicatively connectable to a use's portable electronic device 16 via Bluetooth or other similar wired or wireless communication connection for data transfer.

The data obtained by the user's portable electronic device (for example a mobile phone 16) from the sensor 12 can then be transferred via a telecommunication network to a remote server 20 where it is further processed as described below in more detail.

Optionally, in a separate arrangement (not shown), the processing of the data from the sensors may take place on the portable electronic device, in which case the processing detailed below may be conducted on the portable electronic device without communication to and from a remotely located server 20.

As depicted, the remote server 20 may perform sensor data calibration and real-time gait cycle segmentation for data processing 22, machine learning model 24 and real-time message transmission via a message gateway 26 to the portable electronic deice 16 (optionally using a wireless communication protocol such as a MQTT protocol 28 or similar).

The software application developed for the portable electronic device may have three main functional modules: a Bluetooth Connection module for communicating via Bluetooth 14 (or similar wireless protocol) with the sensor(s), a Sensor Data Display module for visualising predicted KAM and a Server Data transfer module for transferring data to a portable electronic device.

In the embodiment shown, real time data transfer from the portable electronic device to the server may advantageously be performed using MQTT (Message Queuing Telemetry Transport). As is known in the art, MQTT is a publish-subscribe-based protocol and designed for real-time communication between machines. It would be appreciated that other protocols or approaches may be utilised without departing from the present disclosure.

The processed data is inputted into the trained machine learning model on the server 20 (or in an optional embodiment (not shown) on the portable electronic device 16) to predict the KAM for the specific subject during their recent gait cycle(s). The predicted KAM can then be displayed at the use's portable electronic device in real time through an application or similar, optionally as a raw value or as a graphical representation. An alert may be issued to the user where the predicted KAM exceeds a predetermined threshold for one or more gait cycles (e.g. visual, haptic, sound or other means for alerting the user). This alert may then enable the user to subtly adjust their walking to reduce the KAM in the next gait cycle.

The software application may be implemented in JavaScript programming language and configured to connect sensors, receive user's input, send and receive data to and from the server on the portable electronic device 16. It would also be appreciated that other programming languages could be utilised without departing from the scope of the present disclosure for the same purpose.

Figure 2A:
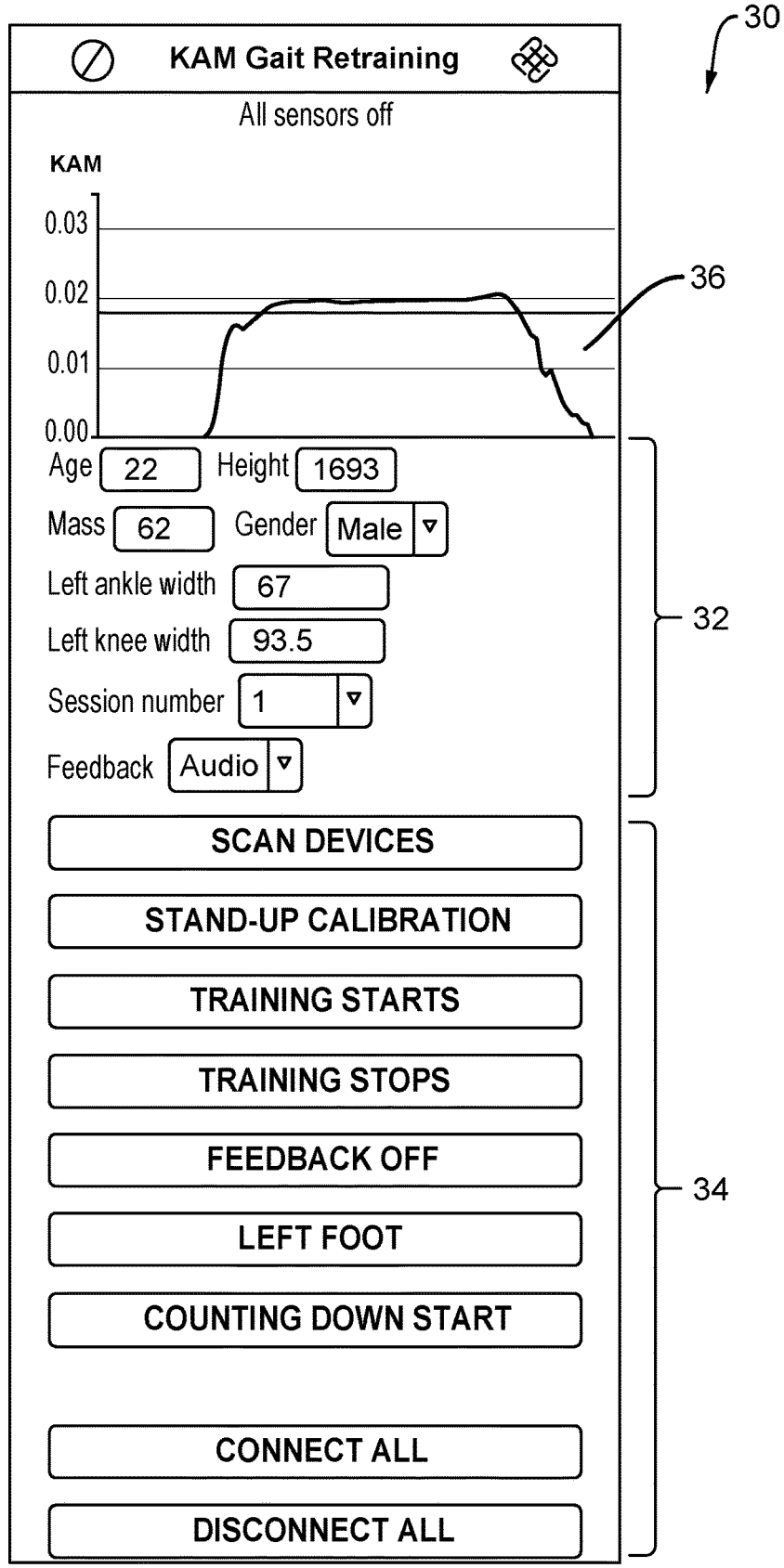
FIG. 2a depicts an exemplary interface for an application on a portable electronic device according to the embodiment depicted in FIG. 1.

FIG. 2a depicts an exemplary graphical user interface 30 for an exemplary application, in this case shown on a portable electronic device 16 such as a mobile phone. A subject's personal information may be specified as shown in the various data entry fields 32. Such personal information may include gender, height, age, mass, information of ankle and knee (for example, ankle width and/or knee width), leg identity (indicating the right leg or the left leg), etc. The ankle and knee information could be useful in calculating angle of knee centre and lower limb orientation, which may affect the KAM prediction. The subject's gender could be another potential factor that influence the KAM. According to a previous study (Webster, K. E., McClelland, J. A., Palazzolo, S. E., Santamaria, L. J., & Feller, J. A. (2012). Gender differences in the knee adduction moment after anterior cruciate ligament reconstruction surgery. Br J Sports Med, 46(5), 355-359), KAM of females are higher because of the size of pelvis differs with gender. Furthermore, the subject's height has a correlations with leg length, and hence knee moment. Further, the subject's weight has a correlation with ground reaction force, an important factor in KAM calculation.

Various operational controls 34 can also be included to specify the various options available to the subject, including scanning active Bluetooth devices, calibrating sensors, starting gait training (enabling the sensors to collect data and starting KAM prediction), stopping gait training (disabling the sensors and ending KAM prediction), various operational settings and similar. The KAM predicted is shown graphically to the subject in the GUI portion 36 shown.

Stored Information

Once trained, the system and method using the neural network taught in the present disclosure may be used for predicting KAM from sensor measurement data by using only sensor data collected for a subject over multiple gait cycles without reference to any measured KAM. In this way a subject's sensor measurement data can be used to predict KAM, potentially in real time, and presented to the subject to allow them to dynamically adjust their gait to reduce their KAM for subsequent gait cycle(s).

In the training process for training the neural network, the present disclosure teaches use of clinical data collected and used to clinically measure KAM; and sensor data collected for the same subject with the same gait cycles in the same time series—i.e., simultaneously. These two types of data which are simultaneously collected are stored. A trained neural network is then able to predict KAM from sensor data obtained for subjects during walking activities, potentially in real time, and in the absence of clinically measured or determined KAM.

It is well known that the standard approach to measuring KAM (external knee adduction moment in the frontal plane) is by using a force plate and a camera motion capture system in a laboratory or clinic environment.

Subjects provided conventionally measured clinical KAM together with sensor data for the purposes of training have diagnosis of knee osteoarthritis and with age range of 62.8±7.3, body height range of 1.62±0.078 m, body weight range 66.9±14.6 kg. Their Kellgren & Lawrence (KL) grade (grade I to VI) were classified based on the X-ray examination result. All subjects are able to walk unaided for at least 10 minutes. The exclusion criteria include contraindications for vigorous physical activities, history of knee surgery, and other injuries that may affect walking gaits.

For each of these subjects during multiple gait cycles, clinically determined KAM was calculated from ground reaction force provided by a force plate and knee joint kinematics captured by a camera motion capture system and tracking reflective markers placed on bony landmarks where the marker set is based on a model described in a previous study (see to Shull, P. B., Silder, A., Shultz, R., Dragoo, J. L., Besier, T. F., Delp, S. L., & Cutkosky, M. R. (2013)).

A 8-camera motion capture system (for example, Vicon, Oxford Metrics Group, Oxford, UK) may be used to record the marker trajectories at 200 Hz (or other appropriate frequencies) when the subjects are walking on a walkway embedded with a force plate (for example, Bertec Corporation, Columbus, Ohio, USA) at their preferred walking speed in three conditions, normal walking, toe-in walking and toe-out walking. Before walking, a 15-min warm-up exercise could be taken (i.e., stretching lower extremities) to assist in the removal of initial noise in the data collected.

Ground reaction force measurements from three axis may be sampled at 1000 Hz (or other appropriate frequencies) and synchronized, for example using Nexus (Vicon, Oxford Metrics Group, Oxford, UK). It would be appreciated that other brands of camera motion capture systems and force plates could be used and other software could be used.

In the described embodiment, measurements including measured KAM and IMU sensor data were obtained from 53 subjects during gait cycles, although it would be appreciated that additional measurements would provide a more detailed library upon which to train the algorithm for predicting KAM, without departing from the present disclosure.

Figure 2B:
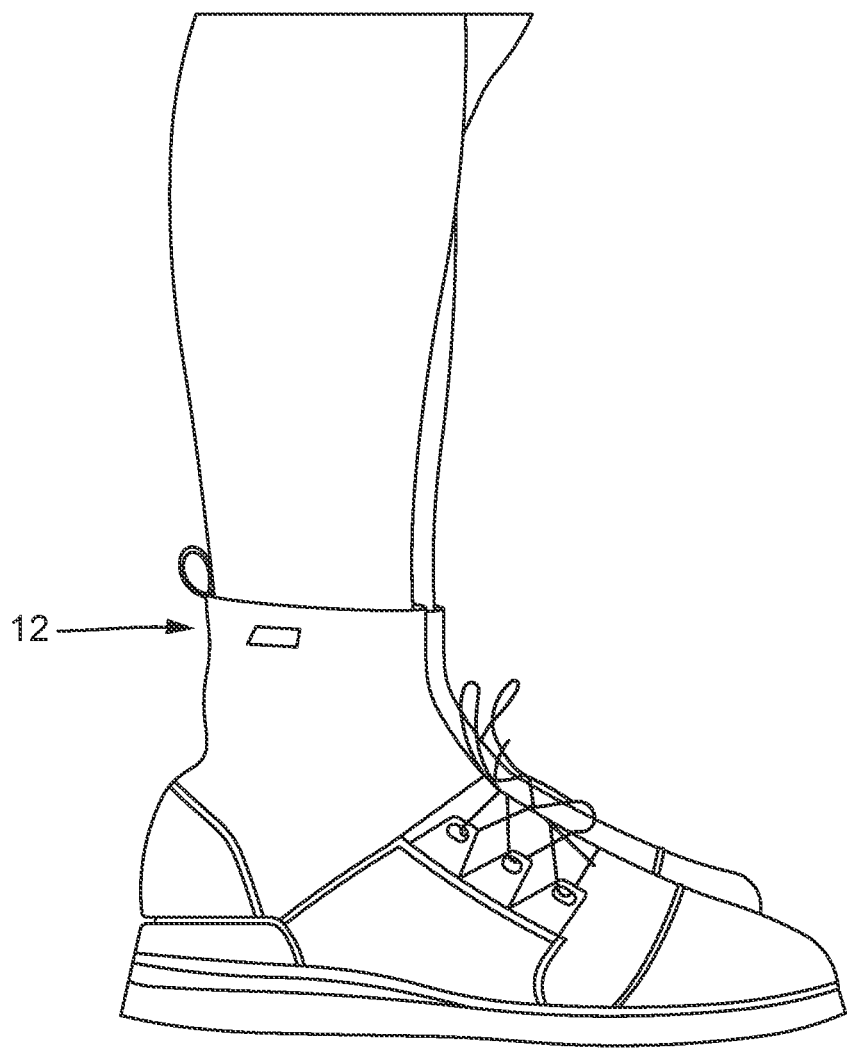
FIG. 2b depicts an exemplary location for the sensors of the embodiment of the disclosure.

FIG. 2b depicts an exemplary locations for the sensor(s) which are located away from the knee joint for which the KAM is being predicted. In the view depicted a wearable sensor 12 is located proximal to the ankle on the lateral side of both feet (although only one foot is visible). Preferably, a sensor may be located at the lateral malleolus level of each leg-preferably on the lateral side although it has been determined that it is also possible to locate the sensors on the medial side.

For the purposes of validating the results obtained from the mass market sensors and research grade sensors we located one of each sensor type on each side of the users malleolus; a total of four sensors per leg. However, in subsequent trials, KAM predictions could be obtained by locating either (and not both) types of sensor proximal the lateral malleolus level, preferably on the lateral side of at least one leg or on the lateral side of each leg. The sensors may be commercially available inertial measurement unit (IMU) sensors for capturing the acceleration and gyroscope data, which may either be research based sensors such as the commercially available NORAXON® slow or fast IMU sensors with increased accuracy and other features, or cheaper mass market IMU sensors such as Bosch BMI 160, iNEMO inertial modules (STMicroelectronics, Switzerland) or SmartBond™ DA14583 sensors (Dialog Semiconductor Reading, UK).

The vertical axis of the IMU sensors is aligned alongside the longitudinal axis of tibia as shown in FIG. 2b. Each sensor 12 can measure the angular velocity and acceleration of an object in three dimensions and can calculate the object's orientation in 3D space.

To verify that the data provided from research grade IMU sensors is comparable to the data obtained from mass market IMU sensors, both inertial measurement unit (IMU) sensors are placed on the same position. In one experiment, the research grade IMU sensors are Noraxon sensors (Range: ±24 g, AZ, USA) and the mass market IMU sensors are SmartBond™ DA14583 sensors (Dialog Semiconductor Reading, UK). The wireless accelerometers of the research grade sensors capture acceleration data at 1000 Hz at each axis, while the mass market IMU sensors capture the acceleration, gyroscope data at a frequency of 100 Hz or other frequency providing sufficient data capture. It would be appreciated that other sensors can be used for the same purpose.

Data Pre-Processing

The accelerometer data and the gyroscope data from IMU sensors may be filtered by low pass filters to reduce high-frequency noises of the system. In the case of SmartBond™ DA14583 IMU sensor, the accelerometer data is filtered by a 40.5 Hz low pass filter and the gyroscope data is filtered by a 39.9 Hz low pass filter, where both the low pass filters are built-in filters for the SmartBond™ DA14583 IMU sensor. It would be appreciated that other low pass filter(s) may be used for the same purpose.

(1) Rotation Matrix

For IMU sensors as is known to persons skilled in the art, there are many sources of error terms and noise in MEMS type accelerometers and gyroscopes.

For example, when combining all axial data, axial error containing axis misalignment can introduce significant errors in sensor fusion, which will make the data inaccurate.

Axial error may be caused when the IMU sensor is attached to a subject's ankle, the angular start position won't be zero and different subjects will have different rotation angle from this start position. Such error will affect the data quality, and add errors during model training.

To remove this axial error, in the start of every experiment, subjects are required to stand naturally and still and then 5 to 8 seconds data is collected as the calibration data. Specifically, the rotation matrix is calculated to transform the IMU sensor plane into a standard plane. The standard plane is defined by local gravity. A simple way to generate a rotation matrix is to composite it as a sequence of three basic rotations. The rotations of the x-, y-, and z-axes of the right-hand Cartesian coordinate system are defined as roll, pitch and yaw rotations, respectively. Because these rotations are expressed as rotations about an axis, their generators were easily expressed.

In three dimensions analysis, rotation can be defined by a single rotation angle and the direction of the unit vector that surrounds it. Therefore, the rotation matrix can be calculated by the following formula:

$$\mathcal{M}(\hat{v}, \theta) = \begin{bmatrix} \cos\theta + (1-\cos\theta)x^2 & (1-\cos\theta)xy - (\sin\theta)z & (1-\cos\theta)xz + (\sin\theta)y \\ (1-\cos\theta)yx + (\sin\theta)z & \cos\theta + (1-\cos\theta)y^2 & (1-\cos\theta)yz - (\sin\theta)x \\ (1-\cos\theta)zx - (\sin\theta)y & (1-\cos\theta)zy + (\sin\theta)x & \cos\theta + (1-\cos\theta)z^2 \end{bmatrix} \quad (1)$$

(2) Gyroscope Zero Drift

Another error source is zero drift which refers to the average output of the gyroscope without any rotation, that is, the deviation from its true value.

For a constant deviation, zero drift causes an angular error that increases linearly with time when integrating and can be obtained by taking the average value of a long-term output when the gyroscope is completely stationary, and then simply subtracting it from the output to compensate.

(3) Stand Phase Segment

As would be appreciated by a person skilled in the art, KAM only exists when there is a contact between the leg and the ground, i.e., stance phase. In order to eliminate unnecessary swing phase parts, which if included could cause abnormal predictions and extra computational burden, and also to give clear and precise feedback to subjects, a real-time segmentation algorithm was implemented.

Figure 3A:
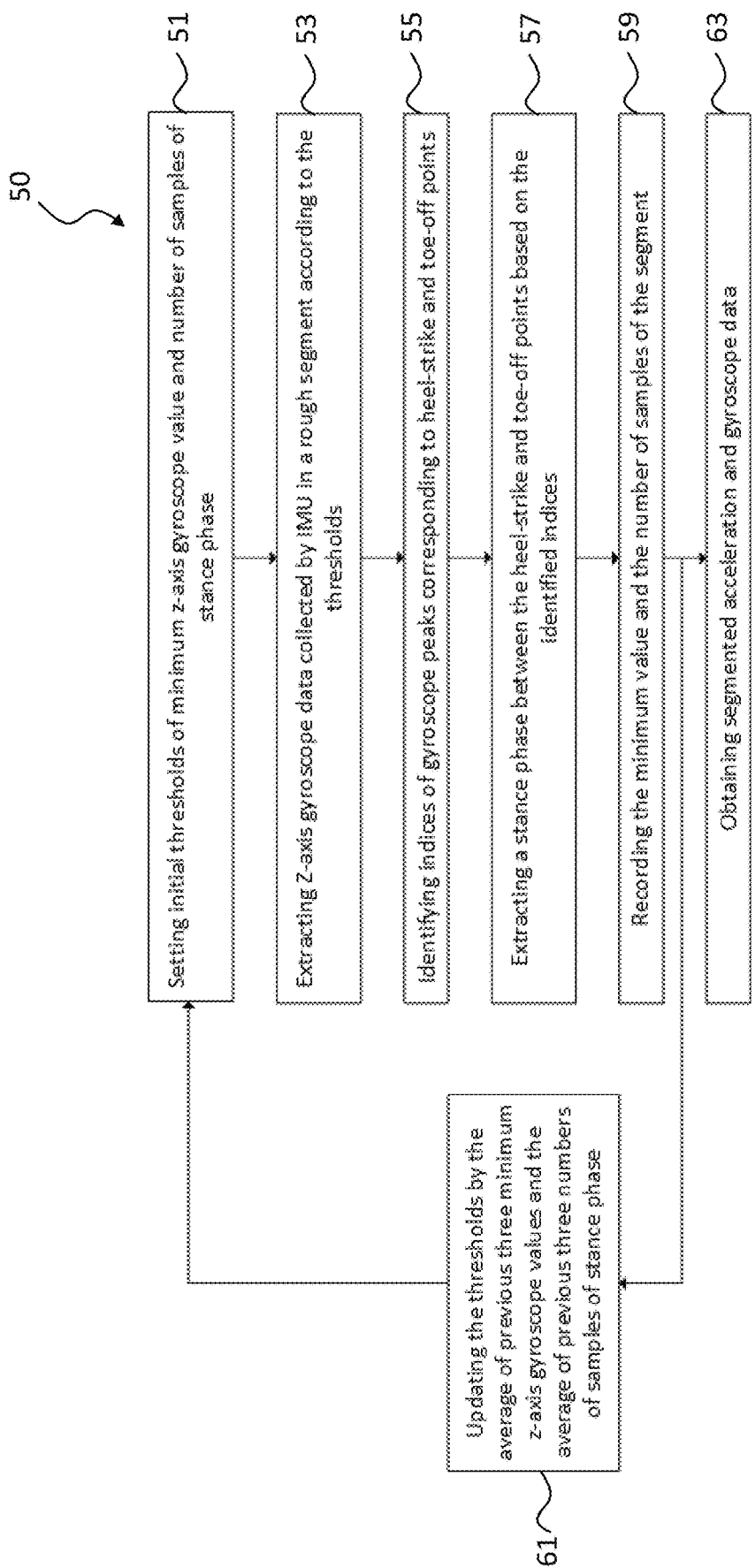
FIG. 3a depicts an exemplary flow chart setting out various stages in pre-processing the data from the sensors before introduction to the machine learning models.

FIG. 3a depicts an exemplary flow chart 50 setting out stages in pre-processing the data from the IMU sensors before introduction of the data to machine learning models, specifically for the stance phase segment.

Step 51: Setting initial thresholds of minimum z-axis gyroscope value and number of samples of stance phase; In the embodiment described, the initial threshold of minimum z-axis gyroscope value is 0 and the initial threshold of number of samples of stance phase is 90.

Step 53: Extracting Z-axis gyroscope data collected by an IMU sensor in a rough segment according to the set thresholds.

Step 55: Identifying indices of gyroscope peaks corresponding to heel-strike and toe-off points.

Step 57: Extracting a stance phase between the heel-strike and toe-off points.

Step 59: Recording the minimum value and the number of samples of the segment.

Step 61: Updating the thresholds by the average of previous three minimum z-axis gyroscope values and the average of previous three numbers of samples of stance phase.

This in effect enables a sliding window average to obtain as a baseline against which subsequent information can be evaluated. More details will be discussed below.

Step 63: Obtaining segmented acceleration and gyroscope data based on the indices obtained from Step 55.

Figure 3B:
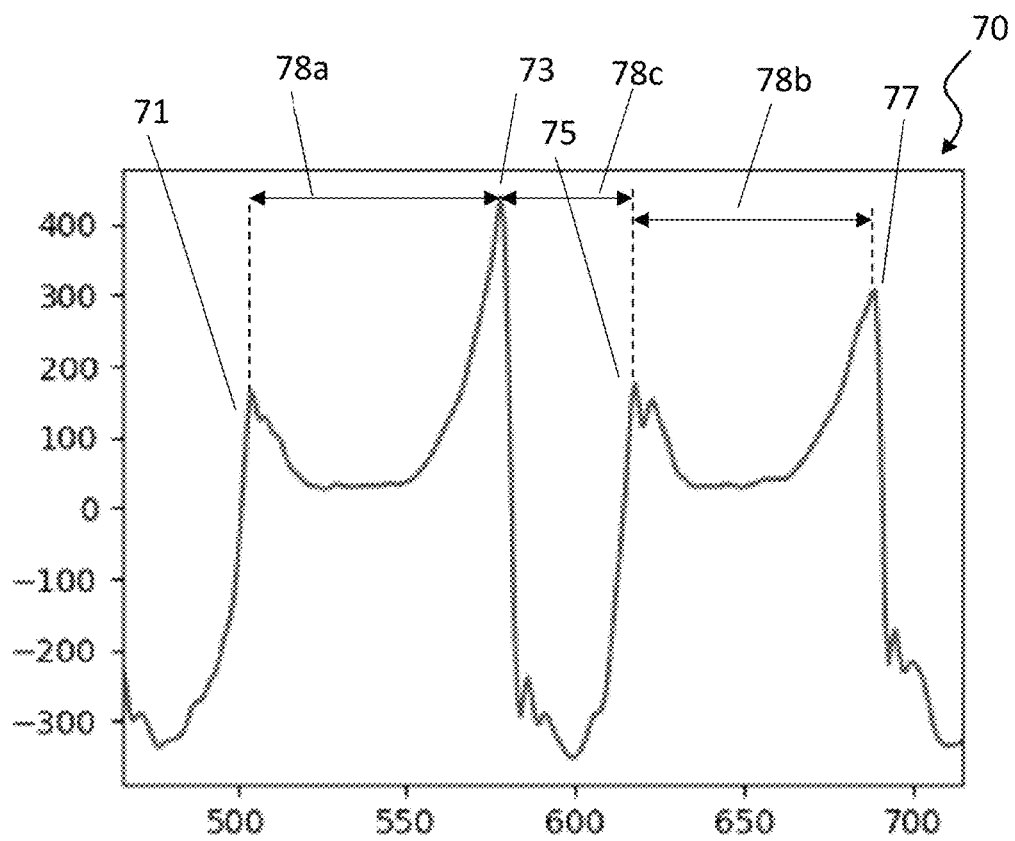
FIG. 3b depicts an exemplary representation of the variation in gyroscope values in gait cycle detected by sensor.

The segmented stance phase data is fed into one or more neural networks for KAM prediction. FIG. 3b depicts an exemplary representation 70 of the variation in gyroscope values in gait cycle detected by the IMU sensors.

Numbers 71, 73, 75, 77 indicate four peaks, in two gait cycles. As is known in the art, peaks 71 and 75 indicate heel-strike while peaks 73 and 77 represent the toe-off part of a subject's gait cycle. The segment 78a between number 71 and 73, as well as the segment 78b between 75 and 77 is the stance phase of each gait cycle and it is the phase which is useful for KAM calculation. The segment 78c between number 73 and 75 is the swing phase. As a result, a real-time segmentation algorithm is implemented using this theory, by only extracting data relating to the stance phase and filling other parts by 0 in the final prediction.

The algorithm adopted feeds all 6 axis IMU sensor data (3-axis accelerometer data and 3-axis gyroscope data) into the prediction module/the trained neural network immediately after the algorithm detects the toe-off points 73, 77 from gyroscopic data, which represents the ending point of stance phase.

To eliminate possible noise which resembles a gait cycle, as well as to fit different walking speeds of different people, limitations and adjustments described below are made to the algorithm, where the "threshold_high" indicates that the algorithm starts collecting data only when data is larger than it (at the beginning of the gait cycle), while the "threshold_low" means the algorithm stops collecting data only when the data drops below it. The "length" is the number of points of a segment. To make the algorithm more adaptable to different people, the average value of the past three steps are set as the new threshold/parameter for the next gait cycle.

$$\text{threshold}_{high}(N+1) = 1/3 \cdot \Sigma_{i=N-2}^{N} \text{threshold}_{high}(i) \qquad (1)$$

$$\text{threshold}_{low}(N+1) = 1/3 \cdot \Sigma_{i=N-2}^{N} \text{threshold}_{low}(i) \qquad (2)$$

$$\text{length}(N+1) = 1/3 \cdot \Sigma_{i=N-2}^{N} \text{length}(i) \qquad (3)$$

$$\text{length}_{high}(N) = \text{length}(N) \times 1.3 \qquad (4)$$

$$\text{length}_{low}(N) = \text{length}(N) \times 0.7 \qquad (5)$$

The stance phase segment obtained by the algorithm based upon IMU sensor data is compared to the stance phase segment using force plate and treadmill, so as to evaluate the accuracy if the gyroscope data only is used to determine the stance phase.

The ratio of stance phase to a combination of swing phase and stance phase is calculated for the evaluation. The ratio for the segment method based on the IMU sensor data is 54% while the ratio regarding the segment method based on the force plate is 63%. Hence, the 54% portion determined from the sensor data potentially covers the segment where KAM peaks lie, which means that the method based on the sensor data to segment the stance phase has an acceptable accuracy.

Modelling and Machine Learning

As discussed, for a specific subject gait cycle in real time, the relationship between KAM and processed sensor data is able to be predicted using a trained machine learning model.

In this disclosure, machine learning models were trained based on XGBoost and artificial neural network (ANN), respectively. It would be appreciated by the person skilled in the art that other machine learning models can be trained based on the collected data for the purpose of KAM predication.

(1) XGBoost

XGBoost is an efficient implementation of gradient boosting algorithm which may be used in machine learning. Gradient boosting seeks to minimize the residuals of all the weak learners by adding a new weak learner. Multiple learners are added together for final prediction, and the accuracy is higher than a single learner. XGBoost is characterized by fast calculation speed and good model performance.

Input features may include acceleration and angular velocity at the ankle(s) of a subject from the sensors, the integral and derivative of acceleration and angular velocity, and subject's height, ankle width of one or both feet. The dataset is split into 80% training dataset, 10% validation dataset and 10% testing dataset. Parameters are tuned by grid search cross validation. For one specific subject, one third of subject's data is added to train the model and the achieved $r^2$ scores of training, validation and test are 0.9951, 0.9473, and 0.9061 respectively.

Figure 4:
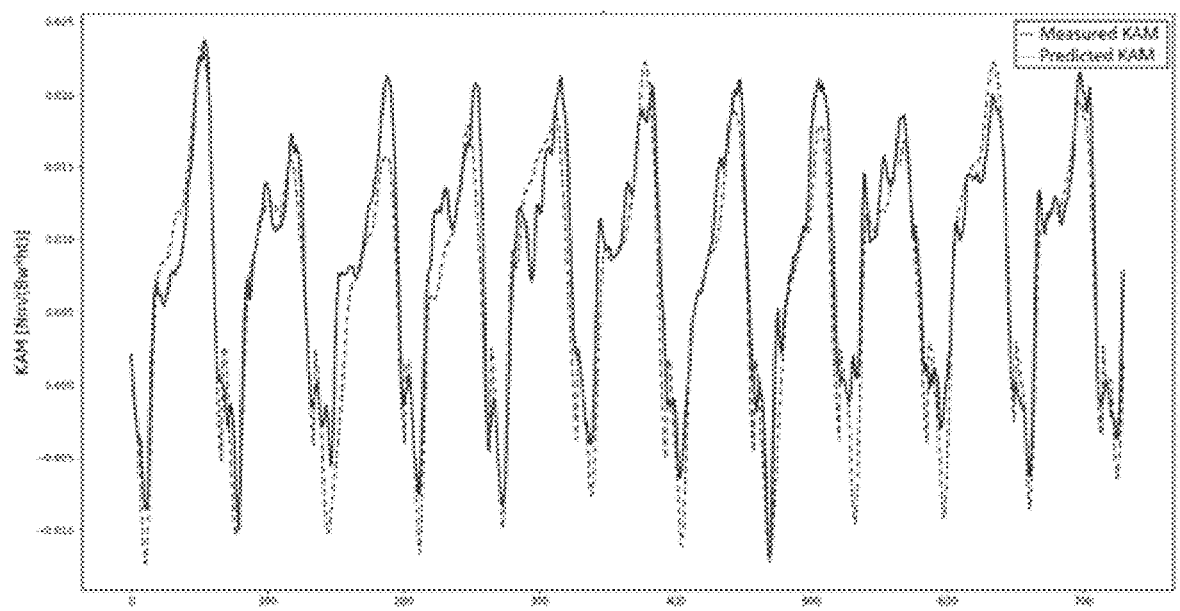
FIG. 4 depicts a graph showing the measured KAM and predicted KAM derived from the system using XGBoost.

FIG. 4 depicts a graph showing the clinically measured KAM and predicted KAM derived from the system using XGBoost. As shown, the pattern and scale of measured KAM and predicted KAM are consistent. It is noted that the predicted KAM is a little "noisier" than the measured KAM curve.

(2) Artificial Neural Network (ANN)

Alternatively, an ANN may also be used with the aim of predicting the KAM curve using the 6 axes IMU sensor data (including 3-axis accelerometer data and 3-axis gyroscope data). The KAM curve includes and represents KAM collected from "toe-out", "toe in", and "normal" configurations. The peak curve shape changes in characteristic ways in these configurations. Typically, for the "toe out" configuration, first peak is higher than the second peak, for "toe in" configuration, second peak is higher than the first peak and for the "normal" configuration, and both peaks are roughly equal. The ANN is used to capture this sensitivity, along with the KAM at those points.

Figure 5A:
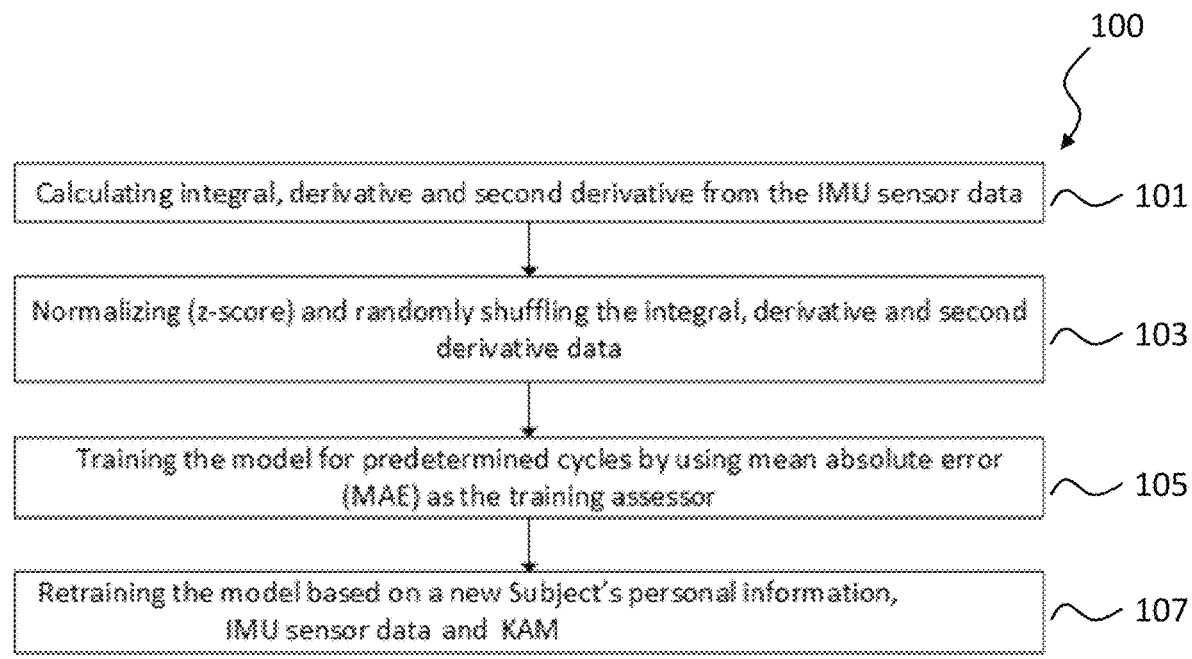
FIG. 5a depicts a schematic flowchart setting out the various stages in an artificial neural network machine learning model.

FIG. 5a depicts a schematic flowchart 100 setting out the various stages in an artificial neural network machine learning model.

Step 101: calculating integral, derivative and second derivative from the IMU sensor data.

Step 103: normalizing (z-score) and randomly shuffling the integral, derivative and second derivative data;

Normalization aims to avoid vanishing gradient problem while training the model and randomly shuffling gives better training results by enhancing uncertainty of the next sample.

Step 105: training the model for predetermined cycles by using mean absolute error (MAE) as the training assessor;

The model is trained based on using the Subject's personal information (such as age, gender, height, body mass, knee width and ankle width), IMU sensor data and measured KAM. In the embodiment described, the model is trained for 1000 cycles (epochs). The architecture of the model will be discussed below. It would be appreciated by a skilled person in the art other model architecture could be used; and that other numbers of cycles could be used for training (1000 cycles is merely exemplary).

After the steps 101 to 105, a trained ANN is obtained and ready for the prediction of KAM. However, a further step 107 may also be undertaken to retrain the ANN so as to improve its adaptability/accuracy, especially if a small initial training data set is utilised. As the size of the data set increases, then the increase in accuracy expected from additional retraining would be less significant.

Step 107: retraining the model based on a new Subject's personal information, IMU sensor data and measured KAM.

The personal information may include age, gender, height, body mass, knee width and ankle width or other relevant subject parameters. Also, the new Subject's IMU sensor data is normalized using mean and standard deviation and randomly shuffled so as to avoid vanishing gradient problem and enhancing uncertainty. After step 107, the trained model can then be used in real time for KAM prediction.

FIGS. 5b1 and 5b2 depict an exemplary architecture 120 of the artificial neural network of FIG. 5a. Inputs of the network are the subject information, 6 axis IMU points and their corresponding integrals, first derivatives and second derivatives respectively. Subject information includes age, gender, height, body mass, knee width and ankle width. Output from the artificial neural network is KAM across time.

As shown, 10 fully connected layers are used with 256 neurons in layers 1 to 6, 128 neurons in layers 7 to 8 and 64 neurons in layers 9 to 10. Typically, the deeper layers have lesser number of neurons to make the mapping smoother. But this is not a standard rule. ReLU (rectified Linear Units) is used as activation function, which is a simple and yet very effective non-linear activation function. Along with normalization, it also helps in preventing the vanishing gradient problem. It can be written as y=max(o,x).

As discussed above, the inputted data for training the ANN include integral and derivatives of the curve. Each point in a gait cycle had a corresponding set of IMU recording features, including the integral and derivatives (first and second) of acceleration and angular velocity recorded. Integral value was calculated from the beginning of each gait cycle up to that point using Trapezoidal integration technique. It is intended to capture the memory of the curve with integration. In addition, an approximated centred discrete derivative was calculated for every point respectively, so that:

$$X'_t = (X_{t+1} - X_{t-1})/2\Delta t \quad (7)$$

In the same way, an approximated centered discrete second order derivative was also calculated so that:

$$x''_t = (x'_{t+1} - x'_{t-1})/2\Delta t \quad (8)$$

In our case, $\Delta t=0.005$ seconds, as it is the smallest possible time we could capture at sampling rate of 200 Hz. First derivative captures the slope of the curve whereas second derivative captures the curvature.

Figure 5C:
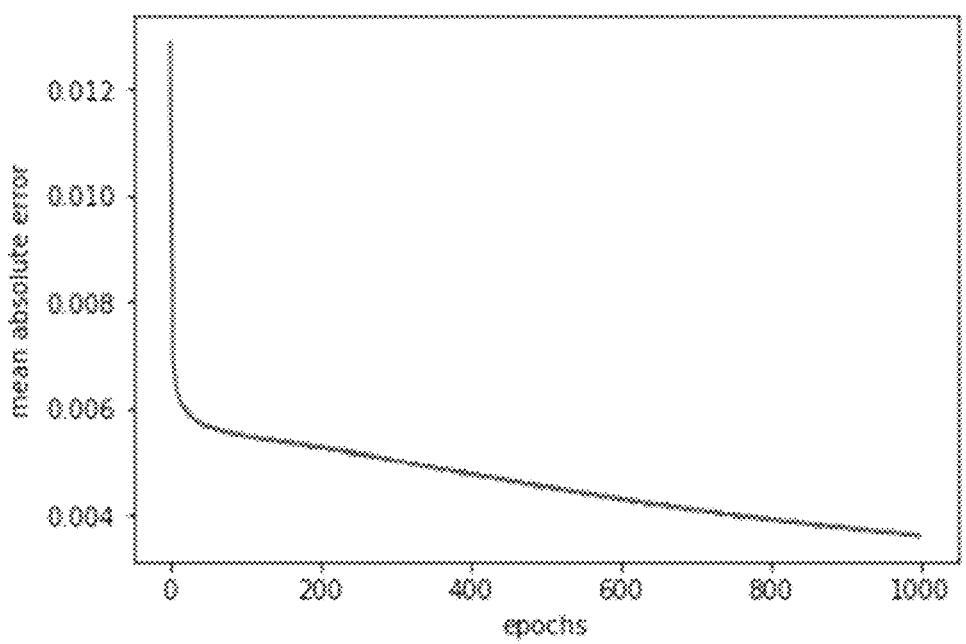

FIG. 5c depicts a training graph for the second exemplary machine learning algorithm of FIG. 5a.

The model is trained on all the available training data which consists of all the trials conducted for data collection using a system including VICON (for measuring KAM) and both research grade and mass market IMU sensors, where the data collected respectively from the research grade IMU sensors and the mass market IMU sensors are synchronised. 735 gait cycles were recorded from 53 subjects. "rmspropoptimizer" is used to train the model with the learning rate of 0.001. Dropout regularization is used for all the layers except the last layer with the dropout value of 0.02. It means that at each epoch, 2% of randomly selected neurons were 'turned off'. This technique prevents overfitting and hence makes the network more generalized. Mean absolute error (MAE) is used to evaluate the training procedure. It is found that r squared and MAE are proportional. The MAE for the general model is 0.004 (less than 20% of average KAM) and is reduced to 0.002 after calibration (less than 10% of average KAM).

Figure 5D:
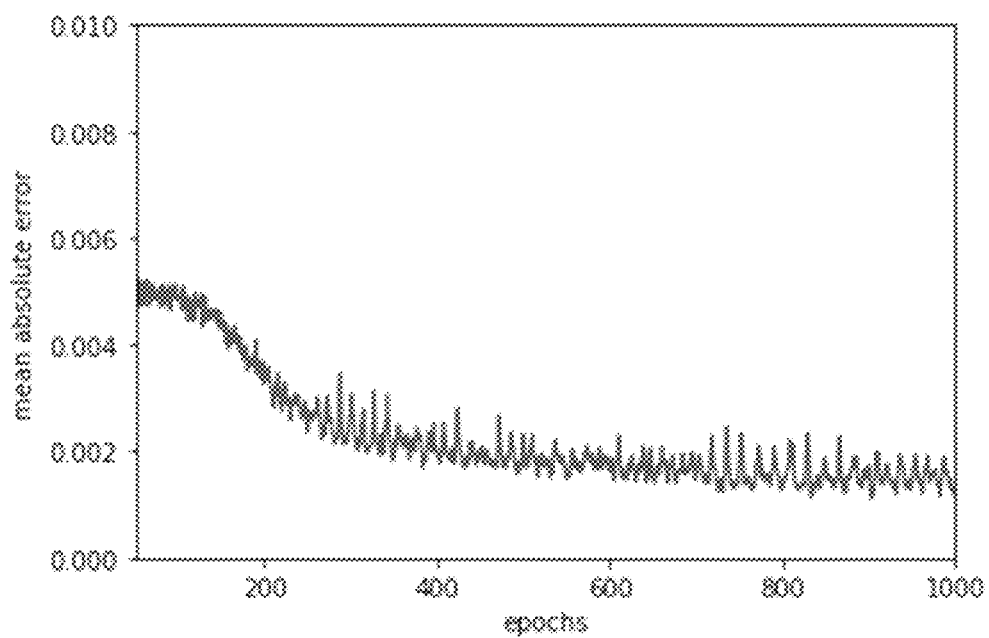

The general model is first trained with all the available training data and retrained based on leave-one-out cross-validation which will discussed in detail later. The calibration curve is shown in FIG. 5d. The curve corresponds to model retraining (MAE) using test subject's data. The curve shown in FIG. 5d is the training curve of this process. Similarly to when training the general model, mean absolute error (MAE) is used as a training assessor and this curve shows how MAE decreases while we keep increasing epochs until a satisfactory value is obtained. When retraining the model the goal is to achieve mean absolute error of less than 10% of the average KAM.

In one exemplary embodiment, leave-one-out cross-validation is conducted with 53 subjects in training data. That means training general model on 52 subjects and using the remaining 1 subject (so called as "test subject") to calibrate and predict. It is appreciated that other validation approaches could be used.

The gait cycles between different subjects may vary greatly. Therefore, even after training the model, to predict the KAM of a new subject with data new to the model, especially if the size of the pre-existing data set is limited, accuracy may be increased by further "calibration" or "adjustment" of the model. In this optional further calibration, the trained model (with the data of all the other subjects) is retrained with some data for the "test" subject.

The performance of the model can also be assessed by using some data for the test subject which is not used in training and thus, determine the theoretical $r^2$ between predicted and measured values before doing actual predictions for that subject's KAM during activity. As would be expected the need for further calibration will be reduced as the dataset increases in size.

Figure 6A:
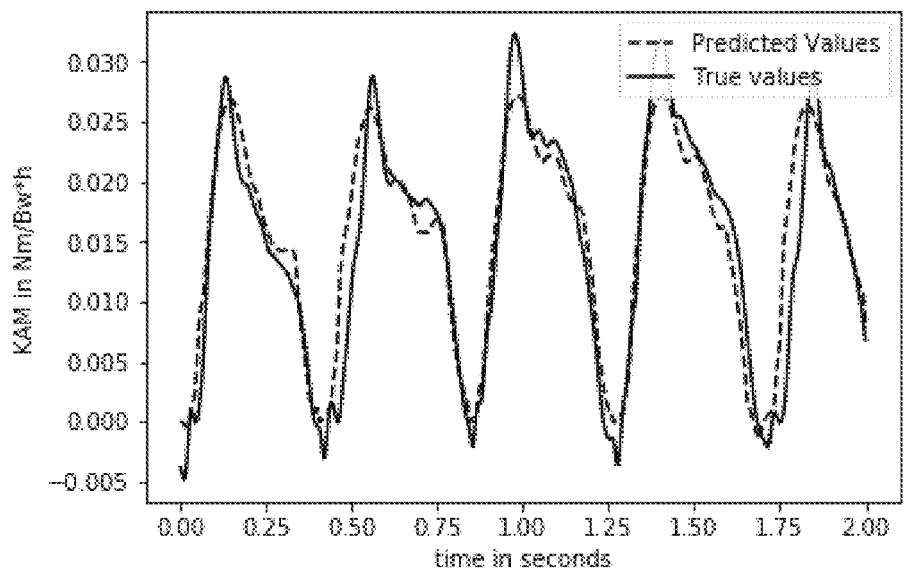
FIG. 6a depicts exemplary results for measured and predicted results for KAM for the exemplary artificial neural network of FIGS. 5a-5d.
Figure 6B:
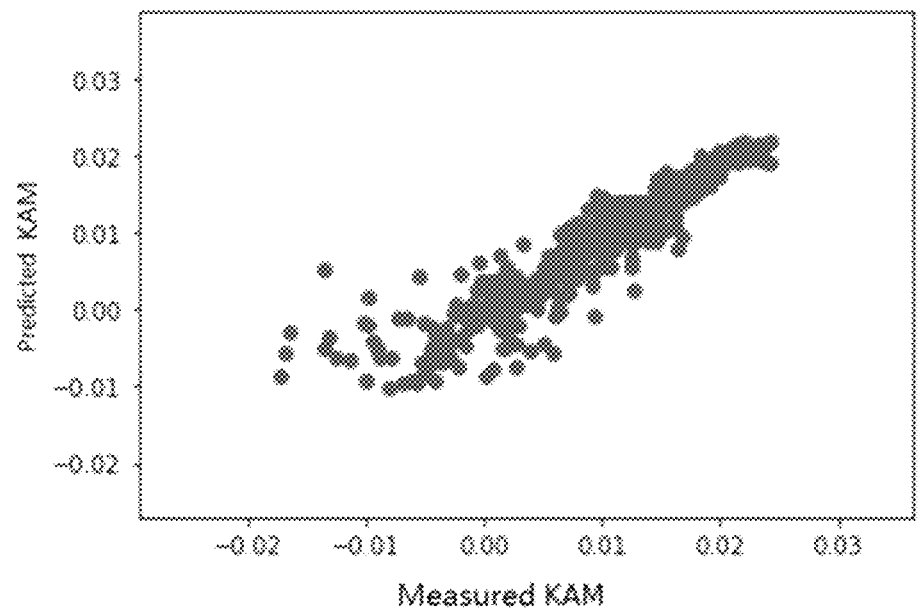
FIG. 6b is another exemplary representation of the actual and predicted results for KAM for the exemplary artificial neural network of FIGS. 5a-5d.

In the embodiment, the general model could be retrained for 1000 epochs with ⅓rd of subject's data (for whom the KAM needs to be predicted) and using ⅔rd of data to evaluate the model. This proportion may be adjusted by the user depending on how much data they have for the individual subject. The key is that there should be enough data to test the model after calibration and to calculate the theoretical $r^2$. This technique can be seen as a variant of transfer learning and was repeated for all the subjects. Resulting $r^2$ of KAM prediction was 0.956±0.031 whereas $r^2$ of the peak was 0.934. Example of predicted KAM vs measured KAM across time for some example trials is shown in FIG. 6a. Predicted and measured KAM of all trials from all subjects are shown in FIG. 6b.

In XGBoost model, importance of various parameters can be determined by the neural network in order to conduct feature selection from within the parameters. XGBoost model uses only 1 feature of the foot data (either ankle width or knee width for example) to predict the KAM for a user; on either or both sides.

The present system, method and software advantageously enables a subject's KAM to be predicted using sensor data received from sensors conveniently fitted proximal the subject's ankle. Previously, the KAM could only be obtained from complex lab settings, including the motion capture system and force plates. Using prior art techniques it is very difficult to obtain KAM outside the laboratory environment. Advantageously, the prediction may be provided to or performed on a portable electronic device of the subject; and may be configured to provide information to a subject in real time as they go about their normal activities.

In an exemplary embodiment, the information may be utilised to issue an alert to the user when the predicted KAM for one or more gait cycles exceeds a predetermined threshold, enabling the user to correct/adjust their gait, preferably prior to the next gait cycle.

Optionally, the sensors used may be commercially available mass market sensors, providing accelerometer and gyroscopic data of the subjects' movements for interpretation by the trained neural network.

Clinically, it has been demonstrated in a laboratory setting that a six-week gait retraining program reduces knee adduction moment, reduces pain, and improves function for individuals with medial compartment knee osteoarthritis. Journal of Orthopaedic Research, 31(7), 1020-1025).

The invention claimed is:

1. A system for predicting the knee adduction moments (KAMs) of a subject for a plurality of gait cycles of the subject, the system comprising:
    a sensor configured to be attachable at an ankle of a leg of the subject for providing accelerometer and gyroscopic data for the plurality of gait cycles of the subject; and
    a processing means configured to:
        receive parameters of the subject and accelerometer and gyroscopic data from the sensor attached at the ankle of the subject,
        evaluate the received parameters, accelerometer data and gyroscope data using a neural network to obtain a KAM for the knee of the leg, wherein the neural network has been trained by determining KAMs for a plurality of gait cycles of a plurality of subjects from measurements during the plurality of gait cycles and parameters from said plurality of subjects, of predicted KAMs for the plurality of gait cycles of the subject.

2. The system according to claim 1 wherein the measurements used for configuring the neural network include the accelerometer data and the gyroscopic data from the sensor and measured KAMs for the plurality of gait cycles of the plurality of subjects.

3. The system according to claim 2 wherein the parameters of the subject and the parameters from the plurality of subjects comprise one or more parameters selected from the group consisting of age, gender, body mass, height, knee width, ankle width, and leg identity.

4. The system according to claim 2 wherein the measured KAMs are determined from kinematic information for each subject of the plurality of subjects over a plurality of gait cycles for said each subject as well as corresponding ground reaction force measurements of said each subject.

5. The system according to claim 1 wherein the sensor is an inertial measurement unit sensor locatable proximal to a level of a malleolus and adjacent to the ankle wherein the inertial measurement unit sensor is configured to provide accelerometer and gyroscopic data during the plurality of gait cycles of the subject.

6. The system according to claim 1 further comprising a portable electronic device for receiving and displaying predicted KAMs to the subject during the plurality of gait cycles of the subject, wherein the portable electronic device is in communication with the processing means.

7. The system according to claim 1 wherein the processing means is further configured to generate a signal to alert the subject when the predicted KAMs during the plurality of gait cycles of the subject exceed a predetermined threshold.

8. The system according to claim 1 wherein the processing means is configured for extracting a plurality of data segments from the accelerometer and gyroscopic data of the sensor between a heel strike and a toe off part of a gait cycle of the plurality of gait cycles of the subject.

9. The system according to claim 1 wherein the predicted KAM for a subject for a gait cycle of the plurality of gait cycles of the subject is outputted from the neural network before a next gait cycle of the plurality of gait cycles of the subject.

10. The system according to claim 1 wherein the neural network is optimised for predicting KAMs for the subject for a further plurality of gait cycles other than the plurality of gait cycles, wherein the neural network is updated by determining KAMs using kinematic information over the plurality of gait cycles for the subject and corresponding ground reaction force measurements and accelerometer and gyroscopic data from the sensor for the subject over the plurality of gait cycles.

* * * * *